US008679508B2

(12) United States Patent
Kim et al.

(10) Patent No.: US 8,679,508 B2
(45) Date of Patent: Mar. 25, 2014

(54) MICROALGAE WITH HIGH-EFFICIENT ABILITY TO REMOVE CARBON DIOXIDE AND USE THEREOF

(75) Inventors: Mi Kyung Kim, Gyeongsangbuk-do (KR); Myung Soo Han, Seoul (KR); Eon Seon Jin, Seoul (KR); Choul-Gyun Lee, Seoul (KR)

(73) Assignee: Ecophyco Tech, Ltd., Gyeongsan (KR)

( * ) Notice: Subject to any disclaimer, the term of this patent is extended or adjusted under 35 U.S.C. 154(b) by 338 days.

(21) Appl. No.: 12/993,447

(22) PCT Filed: May 22, 2009

(86) PCT No.: PCT/KR2009/002724
§ 371 (c)(1),
(2), (4) Date: Nov. 18, 2010

(87) PCT Pub. No.: WO2009/142459
PCT Pub. Date: Nov. 26, 2009

(65) Prior Publication Data
US 2011/0076749 A1  Mar. 31, 2011

(30) Foreign Application Priority Data

May 22, 2008  (KR) .................. 10-2008-0047670

(51) Int. Cl.
*A61K 36/02* (2006.01)
*C12N 1/12* (2006.01)
*A61K 8/02* (2006.01)

(52) U.S. Cl.
USPC .................... 424/195.17; 435/257.1; 424/401

(58) Field of Classification Search
USPC ........................ 424/195.17, 401; 435/257.1
See application file for complete search history.

(56) References Cited

U.S. PATENT DOCUMENTS

| 5,492,938 A * | 2/1996 | Kyle et al. ............. 514/786 |
| 5,597,400 A | 1/1997 | Nonomura et al. |
| 5,846,908 A | 12/1998 | Nonomura |
| 6,121,195 A | 9/2000 | Nonomura |
| 6,602,703 B2 | 8/2003 | Dutil |
| 2003/0073231 A1 | 4/2003 | Dutil |

FOREIGN PATENT DOCUMENTS

| KR | 10-2003-0076133 | 9/2003 |
| KR | 10-0799065 | 1/2008 |

OTHER PUBLICATIONS

Scenedesums producto-capitatus Schumul, entries in Protist Information Server, http://protist.i.hosei.ac.jp/pdb/images/chlorophyta/scenedesmus/producto-capitatus/sp_02.html, 1977 and 2004.*
Komarek J. et al., "Das Phytoplankton Des Süsswassers," pp. 826-827,833,838, and 864, 1983.

(Continued)

*Primary Examiner* — Rosanne Kosson
(74) *Attorney, Agent, or Firm* — Novak, Kim & Lee, PLLC; Jae Youn Kim

(57) ABSTRACT

The present invention relates to microalgae having high efficiency and ability to remove carbon dioxide, and the use thereof. More specifically, the invention relates to *Scenedesmus producto-capitatus* microalgae having high carbon dioxide fixation rate and the use thereof. The microalgae of the invention have a high carbon dioxide fixation rate and excellent resistance even to high concentrations of carbon dioxide, sulfur oxide (SOx) and nitric oxide (NOx) and are rich in biomass, and thus can be advantageously used in formulations for removing carbon dioxide.

1 Claim, 6 Drawing Sheets

(56) References Cited

OTHER PUBLICATIONS

Hegewald, E. et al, "Annotated Catalogue of Scenedesmus and Nomenclaturally Related Genera, Including Original Descriptions and Figures"; 1998 Bibl., Phycol. pp. 404-405.

Parsons, T.R. et al., "Discussion of Spectrophotometric Determination of Marine-Plant Pigments, with Revised Equations for Ascertaining Chlorophylls and Carotenoids" 1963, pp. 155-163.

Kim et al., "Enhanced Production of *Phaeodactylum tricornutum* (Marine Diatoms) Cultured on a New Medium with Swine Wasterwater Fermented by Soil Bacteria"; J. Microbiol. Biotechnol. vol. 16, Jun. 2006, pp. 1947-1953.

Juneau, P. et al., "PAM Fluorometry in the Determination of the Sensitivity of *Chlorella vulgaris, Selenastrum capricornutum*, and *Chlamydomonas reinhardtii* to Copper", Arch. Environ. Contam. Toxicol., 2002, vol. 42, pp. 155-164.

J. Beardall, Abstract of "Photosynthesis and photorespiration in Marine Phytoplankton," Aquatic Botany pp. 105-130, vol. 34., 2003.

L. E. Fridyland, "Models of $CO_2$ concentrating mechanisms in microalgae taking into account cell and chloroplast structure"; Biosystems, 1997, pp. 41-57, vol. 44.

Hale F, et al., "Winkler's Method for the Determination of Oxygen in Water; The Effect of Nitrite and Its Prevention"; The Journal of Industrial and Engineering Chemistry, 1913, pp. 976-980, vol. 12, No. 12.

S. W. Jeffrey et al.; "New Spectrophotometric Equations for Determining Chlorophylls $a, b, c_1$ and $c_2$ in Higher Plants, Algae and Natural Phytoplankton," Biochem. Physiol. Pflanz. 1975, vol. 167, pp. 191-194.

Platt et al., "Photoinhibition of photosynthesis in natural assemblages of marine phytoplankton," J. Mar. Res. 1980, pp. 687-701, vol. 38.

Michael P. Lesser et al., "Effects of UV Radiation on a Chlorophyte Alga (*Scenedesmus* Sp) Isolated from the Fumarole Fields of Mt. Erebus, Antarctica," in J. Phycol, 2002, vol. 38, pp. 473-481.

Hiroshi Takeda, "Cell Wall Sugars of Some Scenedesmus Species," in Phytochemistry, 1996, pp. 673-675, vol. 42, No. 3.

Daniel I. Arnon, "The Light Reactions of Photosynthesis," in Pro. Nat. Acad. Sci. USA, Nov. 1971, pp. 2882-2892, vol. 68, No. 11.

\* cited by examiner

MICROALGAE WITH HIGH-EFFICIENT ABILITY TO REMOVE CARBON DIOXIDE AND USE THEREOF

TECHNICAL FIELD

The present invention relates to microalgae having high efficiency and ability to remove high carbon dioxide removal efficiency, and the use thereof, and more particularly to *Scenedesmus producto-capitatus* microalgae having high carbon dioxide fixation rate and the use thereof.

BACKGROUND ART

With industrial development, the concentration of carbon dioxide in the atmosphere has been increasing due to the consumption of large amounts of fossil fuels, thus increasing global warming. Changes in climate caused by global warming have been responsible for the imbalance of the ecosystem in which the amount of carbon dioxide in the atmosphere is not maintained at a constant level through the carbon cycle, and such changes will be accelerated in future. Hansen and Lebedeff reported an increase in the average temperature of the earth, and general circulation models (GCMs) predict that the surface temperature of the earth will increase. Accordingly, since the international convention on climate change, including a protocol for greenhouse gas reduction, was established, studies on the development of various technologies capable of efficiently removing carbon dioxide are being conducted.

All land plants perform the process of photosynthesis by which the plants synthesize carbohydrates from water and carbon dioxide using solar light as an energy source. In European advanced countries, carbon dioxide is being efficiently recovered by increasing forests using photosynthesis, and forest products are being used in various applications. However, there are a lot of obstacles in removing carbon dioxide using land plants. This is because land plants very slow photosynthetic rates leading to low carbon dioxide fixation rates.

According to reported studies, the use of microalgae (phytoplanktons living in water) allows the fixation rate of carbon dioxide per unit area to be increased by several times to several tens of times. Thus, studies focused on fixing carbon dioxide into starch are being actively conducted.

However, in order to practically use a process of fixing carbon dioxide directly from industrial exhaust gases using a microalgal culture process, the following several problems should first be solved. It is known that industrial exhaust gases have a carbon dioxide content of about 10% for LNG combustion gas or bituminous gas, although the carbon dioxide content varies depending on the type of fuel used. Thus, in order to use microalgae to remove carbon dioxide, the microalgae must be capable of surviving in the above-described range of carbon dioxide content and need to have high carbon dioxide fixation rate. Also, because the exhaust gases contain components inhibiting the growth activity of the microalgae, for example, sulfur oxide (SOx) and nitric oxide (NOx), the microalgae need to have excellent resistance to these components, and also needs to be rich in biomass so that it is industrially used in practice.

Accordingly, it is urgently required to develop microalgae, which have excellent resistance even to high concentrations of carbon dioxide, sulfur oxide (SOx), nitric acid (NOx) and the like and also have a high carbon dioxide fixation rate and are rich in biomass.

BRIEF SUMMARY OF THE INVENTION

The preset inventors have found that *Scenedesmus producto-capitatus* microalgae having a high carbon dioxide fixation rate and excellent resistance even to high concentrations of carbon dioxide, sulfur oxide (SOx) and nitric acid (NOx) and are rich in biomass, thereby completing the present invention.

It is, therefore, an object of the present invention to provide *Scenedesmus producto-capitatus* microalgae, which have a high carbon dioxide fixation rate and are identified by accession number KCTC11336BP.

Another object of the present invention is to provide a formulation for removing carbon dioxide, which contains at least one selected from the group consisting of said microalgae, a culture of said microalgae and a lysate of said microalgae.

Still another object of the present invention is to provide a method of removing carbon dioxide using at least one selected from the group consisting of said microalgae, said culture of microalgae and said lysate of microalgae.

The present invention was made under the support of Gyeongbuk Institute for Marine Bio-Industry (Korea).

To achieve the above objects, the present invention provides *Scenedesmus producto-capitatus* microalgae, which have a high carbon dioxide fixation rate and are identified by accession number KCTC11336BP.

The present invention also provides a formulation for removing carbon dioxide, which contains at least one selected from the group consisting of said microalgae, a culture of said microalgae and a lysate of said microalgae.

The present invention also provides a method of removing carbon dioxide using at least one selected from the group consisting of said microalgae, said culture of microalgae and said lysate of microalgae.

DETAILED DESCRIPTION OF THE INVENTION

Hereinafter, the present invention will be described in further detail.

The *Scenedesmus producto-capitatus* microalgae of the present invention were deposited on May 21, 2008 with the Korean Collection for Type Cultures (KCTC) (Address: Korea Research Institute of Bioscience and Biotechllology (IXBB), Oun-dong, Yusong-gu, Taejon, Korea) under the accession number KCTC11336BP.

With respect to the morphological characteristics of the microalgae of the present invention, four cells form a colony, and the colonies are adjacent to each other in the form of linear or slightly shapes. The cells are slightly convex at the center and are concave toward both ends. The biggest characteristic is that the cell walls at both ends of the cells are thicker or the needle-like tip of the cells is slightly convex and that the cells become circular colonies or oval single cells depending on culture conditions (Komarek J. and Fott, B., 1983. Verl., Stuttgart, 1044 pp).

With respect to the mycological characteristics of the microalgae of the present invention, the microalgae belong to a group of green algae containing chlorophyll a and b, and the cells are single cells and sometimes form colonies. Also, the microalgae have autotrophic microalgae having a photosynthetic function of synthesizing sugar by absorbing solar energy and carbon dioxide from the atmosphere (Hegewald, E. and C. Silva, 1988. Bibl. Phycol., 587 pp).

The microalgae of the present invention have the highest chlorophyll a concentration among freshwater algae, and considering that chlorophyll a is a component of the reaction center complex of photosystem that performs photosynthesis, and the microalgae can effectively fix carbon dioxide necessary for photosynthesis (see Example 1-2). Also, the results of measuring the photosynthetic efficiency of the chlorophyll a of the microalgae of the present invention indicate that the microalgae of the present invention have the highest photosynthetic efficiency among freshwater algae (see Example 1-3). Moreover, the results of measuring the growth rate of the microalgae of the present invention indicate that the highest growth rate among freshwater algae (see Example 1-4). Accordingly, the present inventors believed that the microalgae of the present invention can fix carbon most effectively among freshwater algae and are rich in biomass.

Also, in order to specifically evaluate the carbon dioxide fixation ability of the microalgae of the present invention, a carbon-concentrating mechanism (CCM) experiment was carried, and a P-I curve was plotted. The results of the experiment were assessed using *Chlamydomonas* as model microalgae, and the results of the assessment indicated that the microalgae of the present invention can grow even at a carbon dioxide concentration of about 10% and very effectively perform photosynthesis. Accordingly, the microalgae of the present invention can remove up to 0.88 mg of carbon dioxide per liter of medium on the basis of one day, that is, 880 g of carbon dioxide per ton of medium (see Example 2).

Moreover, the results of examining the change in expression of carbonic anhydrase, an enzyme associated with carbon dioxide fixation of the microalgae of the present invention, indicate that the microalgae of the present invention express carbonic anhydrase at a constant level regardless of the concentration of carbon dioxide, suggesting that the microalgae of the present invention can be effectively cultured even at high carbon dioxide concentrations (se Example 3).

Also, the results of performing the mass culture of the microalgae of the present invention using a photo-bioreactor while evaluating the carbon dioxide fixation ability of the microalgae indicate that the microalgae of the present invention can effectively fix carbon dioxide even at high carbon dioxide concentrations and that the concentration of biomass in the microalgae of the present invention increases with an increase in the concentration of carbon dioxide. Furthermore, the microalgae of the present invention even if a flue gas containing NOx or SOx is supplied (see Example 4).

Accordingly, the microalgae of the present invention have a high carbon dioxide fixation rate and excellent resistance even to high concentrations of carbon dioxide, sulfur oxide (SOx) and nitric oxides and are rich in biomass.

Also, a formulation for removing carbon dioxide according to the present invention comprises at least one selected from the group consisting of said microalgae, a culture of said microalgae and a lysate of said microalgae and can be effectively used to remove carbon dioxide.

Because the microalgae of the present invention has a very high ability to fix carbon dioxide, the formulation for removing carbon dioxide, which contains the microalgae of the present invention, a culture of the microalgae or a lysate of the microalgae can effectively remove carbon dioxide.

The inventive formulation for removing carbon dioxide can be formulated in various forms. Preferably, it can be formulated in the form of, but not limited to, foods, cosmetics or feeds. The inventive formulation for removing carbon dioxide may preferably contain the microalgae of the present invention at a concentration of, but not limited to, $10^6$-$10^8$ cells/mL.

Meanwhile, the *Scenedesmus producto-capitatus* of the present invention, a culture of the microalgae and a lysate of the microalgae can be used to remove carbon dioxide and can also be used in a method of removing carbon dioxide by culturing the microalgae.

The carbon dioxide fixation ability and other activities of the microalgae of the present invention are as described above.

In order to remove carbon dioxide using the microalgae of the present invention, a culture thereof and a lysate thereof, the culture and the microalgae can be introduced into a microalgal reactor and carbon dioxide can be supplied to the reactor while irradiating light, but the scope of the present invention is not limited thereto.

The microalgal reactor that is used in the present invention may be, but not limited to, any photo-bioreactor known to a person of ordinary skill in the art, which is used for the culture of microalgae.

Particularly, the microalgae of the present invention may be cultured in a medium and culture conditions which can be used for the culture of microalgae. In a preferred embodiment, in order to effectively remove carbon dioxide, the microalgae of the present invention are inoculated into conventional BG-11 medium at a concentration of $1 \times 10^6$ cells/ml and irradiated with a light dose of 125 $\mu Em^{-1} s^{-1}$ at 20° C., but the scope of the present invention is not limited thereto. In addition, in order to carry out the microalgae of the present invention so that they are industrially used, a conventional photo-bioreactor may be used. In one Example of the present invention, a 30-L photo-bioreactor (Liflus G P, Biotron, Korea) which has been widely used was used (see Example 4).

Meanwhile, the microalgae formulation of the present invention can be used to remove carbon dioxide and can also be used in a process of removing carbon dioxide.

The activities of the microalgae formulation of the present invention are as described above.

The microalgae of the present invention have a high carbon dioxide fixation rate and excellent resistance even to high concentrations of carbon dioxide, sulfur oxide (SOx) and nitric oxide (NOx) and are rich in biomass, and thus can be advantageously used in formulations for removing carbon dioxide.

BRIEF DESCRIPTION OF THE DRAWINGS

In FIG. 2, 1: *Anabaena variabilis* (BG-11 medium), 2: *Arthrospira* sp. (BG-11 medium), 3: *Calothrix* sp. (BG-11 medium), 4: *Chlorella ellipsoidea* (CHU-10 medium), 5: *Chlorogloeopsis* sp. (BG-11 medium), 6: *Coelastrum microporum* (BG-11 medium), 7: *Coelastrum reticulatum* var.cubanum (BG-11 medium, 8: *Leptolyngbya* sp. (BG-11 medium), 9: *Monoraphidium contortum* (CHU-10 medium), 10: *Scenedesmus acutus* 25 (BG-11 medium), 11: *Scenedesmus bernardii* (BG-11 medium), 12: *Scenedesmus obliquus* (BG-11 medium), 13: *Scenedesmus producto-capitatus* (BG-11 medium), 14: *Spirulina maxima* (CHU-10 medium), 15: *Stigeoclonium* sp. (CHU-10 medium), and 16: *Tetradesmus wisconsinensis* (BG-11 medium).

In FIG. 3, 1: *Anabaena variabilis* (BG-11), 2: *A. variabilis* (BG-11+BM3%), 3: *Chlorogloeopsis* sp. (BG-11), 4: *C.* sp. (BG-11+BM3%), 5: *Scenedesmus bernardii* (BG-11), 6: *S. bernardii* (BG-11+BM3%), 7: *Senedesmus producto-capitatus* (BG-11), 8: *S. producto-capitatus* (BG-11+BM3%), 9: *Tetradesmus wisconsinensis* (BG-11), and 10: *T. wisconsinensis* (BG-11+BM3%).

In FIG. 5, (1): SDS-PAGE (a: 0% $CO_2$, b: 5% $CO_2$, and c: 5% $CO_2$), and (2): results obtained using carbonic anhydrase antibody (a': 0% $CO_2$, b': 5% $CO_2$, and c': 5% $CO_2$).

BEST MODE FOR CARRYING OUT THE INVENTION

Figure 1:
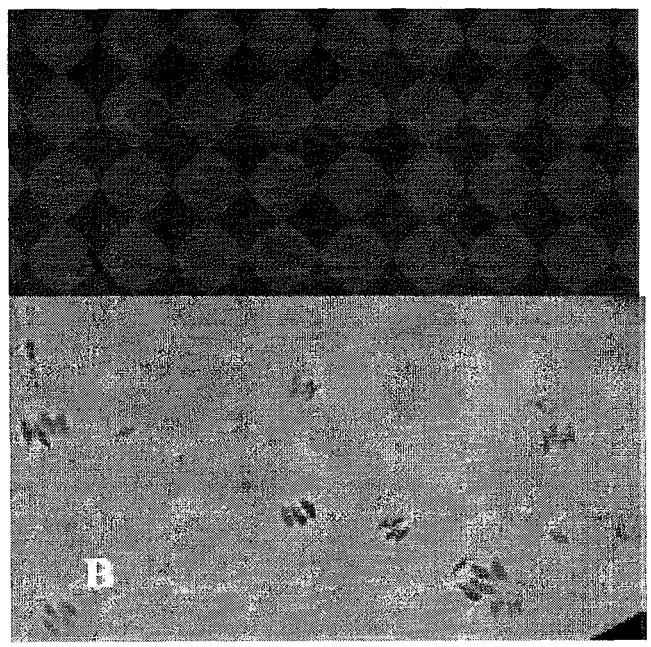
FIG. 1 is a set of photographs showing the results of culturing the microalgae of the present invention in BG11 medium (A; 1000× magnification) and in 80% BM medium (B; 400× magnification).

Hereinafter, the present invention will be described in further detail by way of examples. It is to be understood, however, that these examples are for illustrative purposes and the scope of the present invention are not limited thereto.

Reference Example 1

Compositions of Media Used in the Present Invention
<1-1> Preparation of BG-11 Medium

TABLE 1

Preparation of BG-11 medium

| # | Component | Amount | Stock Solution Concentration | Final Concentration |
|---|---|---|---|---|
| 1 | NaNO₃ (Fisher BP360-500) | 10 mL/L | 30 g/200 mL dH20 | 17.6 mM |
| 2 | K₂HPO₄ (Sigma P3786) | 10 mL/L | 0.8 g/200 mL dH20 | 0.22 mM |
| 3 | MgSO₄•7H₂O (Sigma230391) | 10 mL/L | 0.15 g/200 mL dH20 | 0.03 mM |
| 4 | CaCl₂•2H₂O (Fisher79) | 10 mL/L | 0.72 g/200 mL dH20 | 0.2 mM |
| 5 | Citric Acid H₂O (Fisher A104) | 10 mL/L | 0.12 g/200 mL dH20 | 0.03 mM |
| 6 | Ammonium Ferric Citrate | 10 mL/L | 0.12 g/200 mL dH20 | 0.02 mM |
| 7 | Na₂EDTA•2H₂O (SigmaED255) | 10 mL/L | 0.02 g/200 mL dH20 | 0.002 mM |
| 8 | Na₂CO₃ (Baker 3604) | 10 mL/L | 0.4 g/200 mL dH20 | 0.18 mM |
| 9 | BG-11TrE metals | 1 mL/L | | |
| 10 | Sodium Thiosulfate (agar media only sterile) | 24.8 g/100 mL | | 1 mM |

<1-2> Preparation of CHU-10 Medium

TABLE 2

Preparation of CHU-10 medium

| # | Component | Amount | Stock Solution Concentration | Final Concentration |
|---|---|---|---|---|
| 1 | Chu Stock Solution | 10 mL/L | | |
| 2 | NaHCO₃ (Fisher S 233) | 1 mL/L | 1.26 g/90 Ml | 0.17 mL |

<1-3> Preparation of BG-11+3% BM Medium

3% BM was added to BG-11 to prepare BG-11+3% BM medium. BM is one obtained by fermenting and purifying livestock wastewater, and the particulars thereof are described in Korean Patent Nos. 0500333 and 0799065.

Example 1

Isolation of Microalgae having Excellent Ability to Fix Carbon Dioxide
<1-1> Freshwater Algae Used in the Present Invention The following freshwater algae species known to have a high chlorophyll content and excellent growth activity were obtained from the Korea Plankton Culture Collection for Industrialization (KPCCI), Marine Science Research Center, Yeungnam University, Korea, and isolated according to the type of microalgae: *Anabaena variabilis* (KPCCI docket No. P-F-38); *Arthrospira* sp. (KPCCI docket No. P-F-32); *Calothrix* sp. (KPCCI docket No. P-F-33); *Leptolyngbya* sp. (KPCCI docket No. P-F-36); *Spirulina maxima* (KPCCI docket No. P-F-88); *Chlorella ellipsoidea* (KPCCI docket No. P-F-57); *Chlorogloeopsis* sp. (KPCCI docket No. P-F-34), *Coelastrum microporum* (KPCCI docket No. P-F-11); *Coelastrum reticulatum* var. cubanum (KPCCI docket No. P-F-27); *Monoraphidium contortum* (KPCCI docket No. P-F-62), *Scenedesmus acutus* (KPCCI docket No. P-F-4); *S. bernardii* (KPCCI docket No. P-F-16); *S. obliquus* (KPCCI docket No. P-F-10); *S. producto-capitatus* (KPCCI docket No. P-F-7); *Stigeoclonium* sp. (KPCCI docket No. P-F-78); and *Tetradesmus wisconsinensis* (KPCCI docket No. P-F-8).

<1-2> Measurement of Concentrations of Chlorophyll a in Freshwater Algae

The concentrations of chlorophyll a in the freshwater algae isolated in Example 1-1 were measured.

Figure 2:
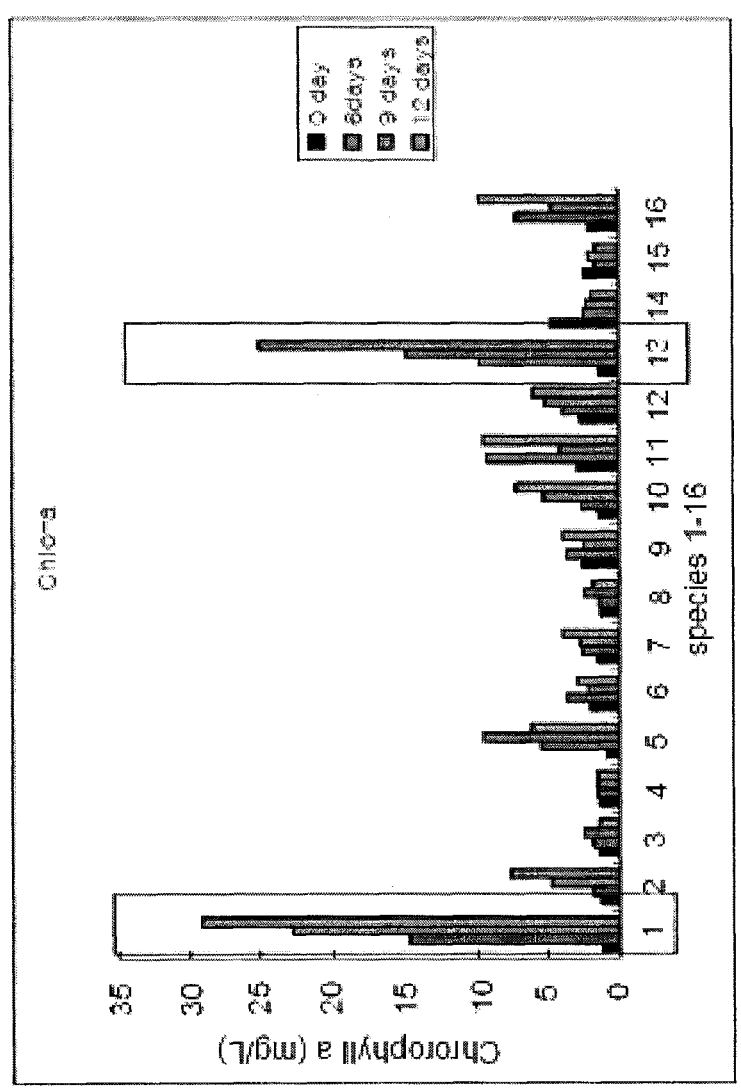
FIG. 2 is a graphic diagram showing the results of measuring and comparing the concentrations of chlorophyll a in freshwater algae.

More specifically, a spectrophotometer was used to calculate the concentrations of chlorophyll a (Parsons T. R. et al., J. Mar. Res., 1963, 155-163, 21). Each of the above microalgae species was inoculated into CHU-10 at a concentration of $1.4 \times 10^6$ cells/ml and cultured by irradiation with a light dose of 125 $\mu Em^{-2}s^{-1}$ at 20° C., and 3 ml of the culture was filtered through glass fiber filter (GF/C, 45 mm). To the filtrate, 10 ml of a mixture of acetone and water (9:1) was added, and the solution was centrifuged at 4000 rpm for 20 min, and then stored overnight in a dark place at 4° C. After the centrifugation, a portion of the supernatant was placed in an absorption cell, and the absorbance thereof was measured using a spectrophotometer (Cary 50 Conc, Varian, USA). Herein, the absorbance was measured at 663 nm, 645 nm, 630 nm and 750 nm using a mixture of acetone and water (9:1) as a control, and the concentration of chlorophyll was calculated according to the following equation 1 using the Standard Methods (APPA 1995) (Kim and Chang 2006, J. Microbiol. Biotechnol. 16: 1947-1953). The concentration of chlorophyll a in each of the microalgae was measured, and the results of the measurement are shown in FIG. 2.

$$\text{Chlorophyll a (g L}^{-1}\text{)=amount (ml) of } Y_s \text{ supernatant/amount (L) of filtered sample} \quad \text{[Equation 1]}$$

where $Y_s$=amount (µg/ml) of chlorophyll a=11.64 X1−2.16 X2+0.10 X3;

X1=OD663−OD750;

X2=OD645−OD750; and

X3=OD630−OD750.

As shown in FIG. 2, the *Scenedesmus producto-capitatus* microalgae showed the highest chlorophyll a concentration regardless of the culture period. This suggests that the *Scenedesmus producto-capitatus* microalgae of the present invention have excellent dark reaction activity of fixing carbon dioxide, because a higher chlorophyll a concentration means a larger amount of the component of reaction center complex of photosystem that perform photosynthesis (Juneau, P., A. El Berdey, and R. Popovic. 2002. *Arch. Environ. Contam. Toxicol.* 42: 155-164).

<1-3> Photosynthetic Efficiencies of Chlorophyll a of Freshwater Algae

Figure 3:
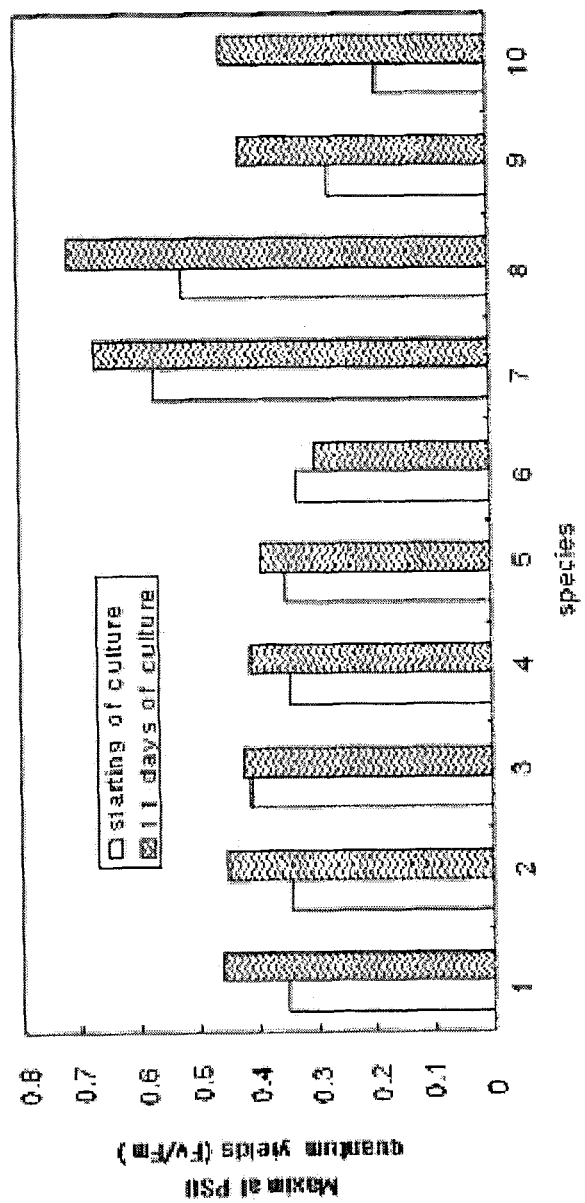
FIG. 3 is a graphic diagram showing the results of measuring and comparing the photosynthetic efficiencies of freshwater algae.

Each of the freshwater algae of Example 1-1 was cultured in BG-11 medium and BG-11+3% BM medium, and the photosynthetic efficiency thereof was measured using a fluorometer (Phyto-PAM, Walz, Germany). Specifically, the photosynthetic efficiency of photosystem II (PS II) was measured at 470 nm. More specifically, the photosynthetic efficiency was determined by calculating the ratio of the maximum variable fluorescence (Fv) to the maximum value of fluorescence (Fm), Fv/Fm, as shown in the following equation 2. A higher Fv/Fm ratio indicates a higher photosynthetic efficiency. The results of the measurement are shown in FIG. 3.

$$Fv/Fm=(Fm'-Ft)/Fm'=dF/(Ft+dF) \quad \text{[Equation 2]}$$

where

Fv/Fm: the maximal PSII quantum yield;

dF: the increase in fluorescence yield;

Ft: the momentary level of fluorescence yield;

Fm': the maximal fluorescence yield.

As can be seen in FIG. 3, the *Scenedesmus producto-capitates* microalgae showed the highest photosynthetic yield regardless of the culture period. Thus, it is believed that the microalgae can most effectively fix carbon dioxide necessary for photosynthesis.

<1-4> Measurement of Growth Rates of Freshwater Algae

5% Bacterial mineral water (BWM, obtained by fermenting granite, pumice, humus soil and microalgae) was added to the CHU-10 medium of Example 1-2 or the BG-11 medium of Example 1-3 >₀] BG-11 and inoculated with each of the freshwater algae of Example 1-2. The inoculated freshwater algae were cultured under a constant light/dark cycle (14 hr light and 10 hr dark) at 22° C. at a light dose of 140 µmolm-$2^{s-}1^{-2}$. At intervals of 2-3-days after the start of the culture, the sample was measured for absorbance at 750 nm using a spectrophotometer, and based on the measured absorbance, the cell division rate (r) of the sample was calculated according to the following equation 3. The results of the measurement are shown in Table 4 below.

$$r=\log_2(N_1/N_o)/t_1-t_0 \quad \text{[Equation 3]}$$

where $N_o$: initial absorbance at 750 nm;

$N_1$: final absorbance at 750 nm;

$t_0$: initial day of culture; and $t_1$: final day of culture.

TABLE 3

Comparison of changes in cell growth rates of microalgae cultured for 13 days (—: less than 0.01)

| Species | Media | Growth rates* | Chl.a (mg/L) | Quantums |
|---|---|---|---|---|
| *Anabaena variabilis* | BG-11 | 0.46 | 9.77 | 0.45 |
| *Arthrospira* sp. | BG-11 | 0.21 | 7.62 | 0.55 |
| *Calothrix* sp. | BG-11 | — | 2.45 | 0.27 |
| *Chlorella ellipsoidea* | CHU-10 | — | 1.58 | 0.06 |
| *Chlorogloeopsis* sp. | BG-11 | 0.27 | 9.13 | 0.51 |
| *Coelastrum microporum* | BG-11 | — | 2.98 | 0.54 |
| *Coelastrum reticulatum* var.*cubanum* | BG-11 | 0.06 | 3.94 | 0.58 |
| *Leptolyngbya* sp. | BG-11 | — | 2.88 | 0.06 |
| *Monoraphidium contortum* | CHU-10 | — | 3.97 | 0.37 |
| *Scenedesmus acutus* | BG-11 | 0.2 | 7.2 | 0.52 |
| *Scenedesmus bernardii* | BG-11 | 0.31 | 9.54 | 0.38 |
| *Scenedesmus obliquus* | BG-11 | 0.34 | 6.04 | 0.5 |
| *Scenedesmus producto-capitatus* | BG-11 | 0.82 | 15.11 | 0.59 |
| *Spirulina maxima* | CHU-10 | — | 3.95 | 0.1 |
| *Stigeoclonium* sp. | CHU-10 | — | 2.62 | 0.1 |
| *Tetradesmus wisconsinensis* | BG-11 | 0.42 | 9.78 | 0.38 |

TABLE 4

Comparison of changes in cell growth rates of microalgae cultured for 11 days (—: less than 0.01)

| Species | Media | Growth rates | Chl a (mg/L) |
|---|---|---|---|
| *Anabaena variabilis* | BG-11 | 0.44 | 7.55 |
| *Anabaena variabilis* | BG-11 + BM6% | 0.71 | 13.2 |
| *Chlorogloeopsis* sp. | BG-11 | 0.18 | 2.71 |
| *Chlorogloeopsis* sp. | BG-11 + BM6% | 0.54 | 3.07 |
| *Scenedesmus bernardii* | BG-11 | 0.77 | 5.59 |
| *Scenedesmus bernardii* | BG-11 + BM6% | — | 3.3 |
| *Scenedesmus producto-capitatus* | BG-11 | 0.96 | 18.6 |
| *Scenedesmus producto-capitatus* | BG-11 + BM6% | 0.87 | 10.91 |
| *Tetradesmus wisconsinensis* | BG-11 | — | 8.78 |
| *Tetradesmus wisconsinensis* | BG-11 + BM6% | 0.64 | 7.3 |

As shown in Tables 3 and 4 above, the Scenedesmus producto-capitatus microalgae (KCTC 11336BP) of the present invention had high chlorophyll a concentration, excellent efficiency of chlorophyll a photosynthesis, indicating excellent carbon dioxide fixation ability, compared to other freshwater algae, and also showed high cell growth rates, suggesting that the microalgae of the present invention can be advantageously used in industrial applications.

<1-5> Identification of *Scenedesmus producto-capitatus* Microalgae of the Present Invention A. Identification method

*Scenedesmus* sp. microalgae live in mud puddles, rivers, marshy land and wet soil and have a crescent-like or oval appearance. 2, 4 or 8 cells are adjacent to each other in a line or arranged in a circular array or two lines. Particularly, each cell is smooth or has long thorns at the tip. Each cell has short thorn, tooth-like protrusions and ridges. Furthermore, in the case of the *Scenedesmus producto-capitatus* microalgae, four cells form a colony, and the colonies are adjacent to each other in the form of linear or slightly shapes. The cells are slightly convex at the center and are concave toward both ends. The biggest characteristic is that the cell walls at both ends of the cells are thicker or the needle-like tip of the cells is slightly convex and that the cells become circular colonies or oval single cells depending on culture conditions.

Based on the above-described morphological characteristics, the present inventors identified the *Scenedesmus producto-capitatus* microalgae of the present invention by mounting a reflector on a microscope, sketching the appearance of species reflected on background paper and comparing the appearance with the above-described characteristics. Particularly, FIG. 1 shows a micrograph of the microalgae of the present invention, and in FIG. 1, "A" (1000× magnification) is a photograph showing the case in which nutrient sources are abundant in BG11 medium, and "B" (400× magnification) is a photograph showing a case in which nutrient sources are deficient in 80% BM medium so that single cells form crescent-like colonies.

B. Deposit

The *Scenedesmus producto-capitatus* microalgae identified as described above were deposited on May 21, 2008 with the Korean Collection for Type Cultures (KCTC) (Address: Korea Research Institute of Bioscience and Biotechllology (IXBB), Oun-dong, Yusong-gu, Taejon, Korea) under the accession number KCTC11336BP.

Example 2

Evaluation of Carbon Dioxide Fixation Ability of Inventive Microalgae

In order to effectively carbon dioxide using microalgae, it is required to measure the photosynthesis rates of the microalgae according to the concentration of carbon dioxide. For this purpose, the present inventors performed a carbon dioxide absorption experiment or carbon-concentrating mechanism (CCM) experiment at various carbon dioxide concentrations and plotted a P-I curve.

<2-1> Evaluation of Carbon Dioxide Fixation Ability at Various Carbon Dioxide Concentrations Carbon dioxide necessary for photosynthesis was artificially introduced at various concentrations. In a control group not artificially introduced with carbon dioxide and in the cases in which carbon dioxide was introduced at concentrations of 5% and 10%, the carbon dioxide absorption of the inventive microalgae was measured according to a conventional method, and the results of the measurement are shown in FIG. 4.

Figure 4:
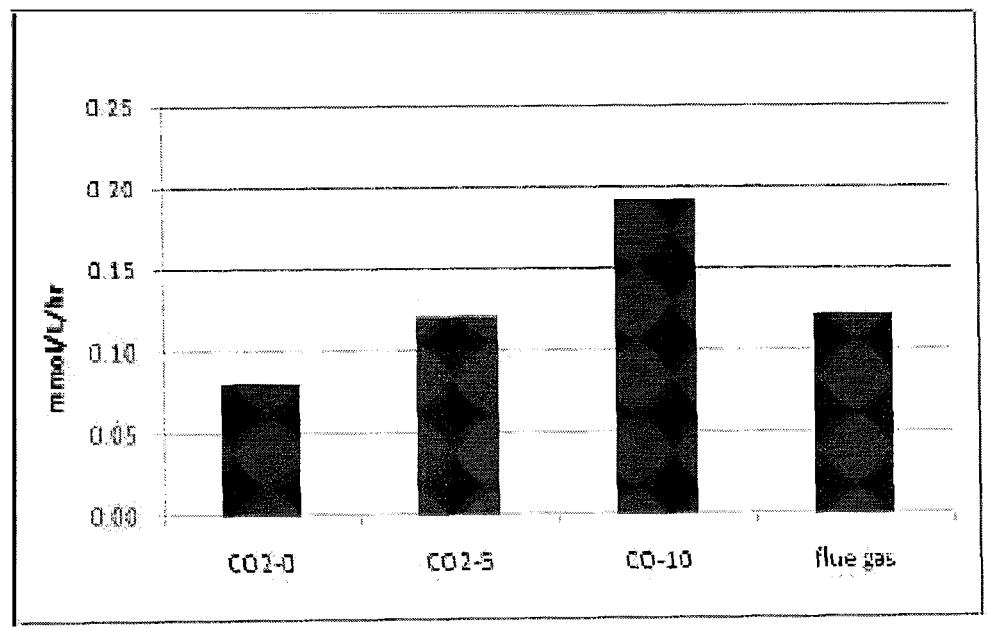
FIG. 4 is a graphic diagram showing the results of measuring the absorption of carbon dioxide by the *Senedesmus producto-capitatus* microalgae of the preset invention at various carbon dioxide concentrations.

As shown in FIG. 4, it could be seen that the microalgae of the present invention could absorb and fix carbon more effectively when a high concentration (10%) of carbon dioxide was present.

<2-2> CCM Experiment

The *Scenedesmus producto-capitatus* microalgae of the present invention were inoculated into BG11 medium and pre-cultured under a 12-hr light/12-hr dark cycle at 25° C. At this time, the concentration of carbon dioxide was set at each of 0.035%, 5% and 10%. Then, in order to completely remove carbon dioxide from the pre-cultured microalgae, the microalgae were inoculated into BG11 medium containing no carbon dioxide, and then placed in 60-ml oxygen bottles. After that, the microalgae were cultured for 3 hours, and the change in concentration between before and after the culture was measured. Based on the oxygen concentrations measured before and after the culture, photosynthetic rate was measured at inorganic carbon concentrations of 0, 0.2, 0.6, 1.2 and 4 mM. The results of the measurement are shown in Table 5 below.

TABLE 5

Results of CCM experiment

| | $CO_2$ condition | | |
|---|---|---|---|
| | 0.035% | 5% | 10% |
| Vmax (mgO$_2$/mgchl.a/hr.) | 19.64 | 33.92 | 36.56 |
| Km (DIC) (Mm) | 0.02 | 0.03 | 0.31 |
| CCM Switch (ON or OFF) | ON | ON | OFF |

As shown in Table 5 above, as the carbon dioxide concentration during the pre-culture was increased, the Vmax value was increased, and when the concentration of carbon dioxide was 0.035-5%, the Km value was maintained at a constant level, but when the concentration of carbon dioxide was 10%, the Km value was very high. Such results suggest that the microalgae of the present invention express CCM at a carbon dioxide concentration of 0-5%, but do not express CCM at a carbon dioxide concentration of 10%. Particularly, it could be seen that, when a high concentration of carbon dioxide is present, the microalgae of the present invention can absorb and remove carbon dioxide in an amount higher than the limit value due to the non-expression of CCM (J. Beardall 1989, Aquatic Botany, 34: 105-130), because CCM is a mechanism of adjusting carbon dioxide fixation enzyme and means a adjuster capable of adjusting and maintaining the limit value to which carbon dioxide can be absorbed (L. E. Fridlyand 1997 Biosystems, 44: 41-57).

<2-3> P-I Curve

To plot a P-I curve, photosynthetic rate was measured at various light doses. The photosynthetic rate was determined by measuring the generation of oxygen using a 60-ml oxygen bottle according to the Winkler method (Hale and Melia 1913. Ind. Eng Chem. 5: 976-980).

The *Scenedesmus producto-capitatus* microalgae of the present invention were divided into three groups, and each group was cultured for 3 hours while the generation of oxygen was measured. During the culture, light dose was set at 0, 30, 60, 120, 220 and 340 μmol photons m$^{-2}$sec$^{-1}$. Also, 50 ml of the culture of the *Scenedesmus producto-capitatus* microalgae of the present invention were filtered through a GF/F filter, and the filtrate was stored with 90% acetone in dark conditions for 24 hours at 4° C., and then the concentration of chlorophyll a in the stored sample was measured using a spectrophotometer (Jeffrey and Humphrey 1975 Biochem.

Physiol. Pflanz 167: 191-194). The photosynthetic rate was evaluated based on the amount of light saturated, according to the Platt's model (Platt et al., 1980, J. Mar. Res. 38: 687-701).

TABLE 6

Results of P-I curve

| | $CO_2$ condition | | |
|---|---|---|---|
| | 0.035% | 5% | 10% |
| Max. rate ($mgO_2$/mgchl.a/hr.) | 38.89 | 36.03 | 55.59 |
| Alpha slope ([$mgO_2$/mgchl.a/hr]/[μE/$m_2$/sec]) | 0.80 | 1.22 | 3.44 |
| Beta slope ([$mgO_2$/mgchl.a/hr]/[μE/$m_2$/sec]) | 0.04 | 0.07 | −0.06 |

As can be seen in Table 6 above, the photosynthetic rate of the *Scenedesmus producto-capitatus* microalgae was saturated at 80-120 $\mu Em^{-2}sec^{-1}$ (Platt et al., 1980, J. Mar. Res. 38: 687-701).

<2-3> Evaluation of Carbon Dioxide Fixation Ability

In order to the carbon dioxide fixation ability of the photosynthetic rate of the *Scenedesmus producto-capitatus* microalgae of the present invention on the basis of the results of Example 2-2 and Example 2-3, the Vmax and Km values of the microalgae of the present invention were compared with those of *Chlamydomonas* used as model microalgae, and the results are shown in Table 7 below.

TABLE 7

Comparison of photosynthetic parameters between inventive microalgae and *Chlamydomonas* microalgae

| | | CO2 condition | | |
|---|---|---|---|---|
| | | 0.035% | 5% | 10% |
| Vmax ($mgO_2$/mgchl.a/hr.) | *Chlamydomonas* (10° C.) | 7.83 | 8.05 | — |
| | *Scenedesmus* (25° C.) | 19.64 | 33.92 | 36.56 |
| Km (DIC) (mM) | *Chlamydomonas* (10° C.) | 0.10 | 1.30 | — |
| | *Scenedesmus* (25° C.) | 0.02 | 0.03 | 0.03 |

As can be seen in Table 7 above, the *Scenedesmus producto-capitatus* microalgae of the present invention expressed CCM even at a relatively high carbon dioxide concentration and had a very high Vmax value. Based on such results, the amount of carbon dioxide which can be removed by the microalgae of the present invention on the basis of one day was measured. As a result, it was confirmed that the microalgae can remove up to 0.88 mg of carbon dioxide per liter of medium on the basis of one day, that is, 880 g of carbon dioxide per ton of medium on the basis of one day.

Example 3

Figure 5:
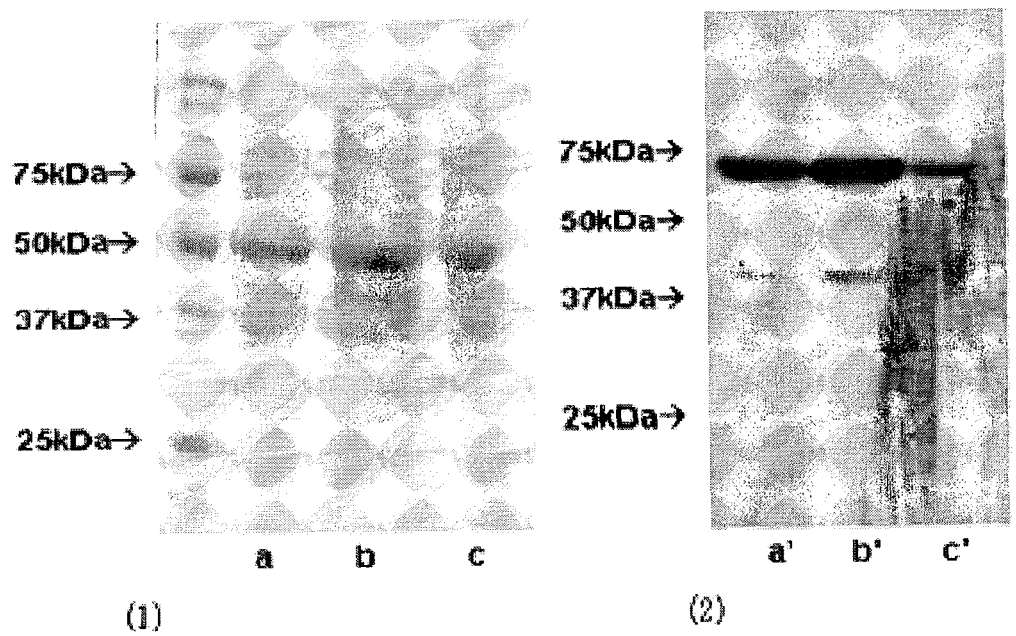
FIG. 5 shows the results of performing Western blot analysis using carbonic anhydrase antibody in order to measure the change in expression of carbonic anhydrase in the microalgae of the present invention.

Change in Expression of Carbonic Anhydrase in Microalgae of the Present Invention The change in expression of carbonic anhydrase which is an enzyme associated with the carbon dioxide fixation of microalgae was examined, and based on the examination results, the carbon dioxide fixation of the present invention was additionally examined. The change in expression of the enzyme was examined using *Dunaliella* sp. as model microalgae. Specifically, using the expressed sequence tag (EST) of the *Dunaliella* microalgae, a carbonic anhydrase sequence was obtained, and based on the obtained sequence, carbonic anhydrase antibody was constructed. To examine the expression pattern of carbonic anhydrase using the constructed antibody, Western Blotting was performed. For this purpose, the protein of the antibody was separated according to size using SDS-PAG and stained with Coomassie brilliant blue dye as a loading control, whereby the protein was determined to be an about 50 kDa protein. FIG. 5 shows the results of the Western blotting.

As can be seen in FIG. 5, when the concentration of carbon dioxide was 5%, the expression of carbonic anhydrase in the microalgae of the present invention rapidly decreased, and this was believed to be because a large amount of carbon dioxide was supplied so that the expression of carbonic anhydrase was not needed.

In order to examine the expression pattern of carbonic anhydrase using the extracted protein, Western blotting was additionally performed. For this purpose, the protein was separated according to size and quantified using Bradford solution as a loading control, and a standard curve was plotted using BSA (bovine serum albumin). Based on the standard curve, the quantified proteins were loaded onto the respective lines. The results of the Western blotting are shown in FIG. 6.

Figure 6:
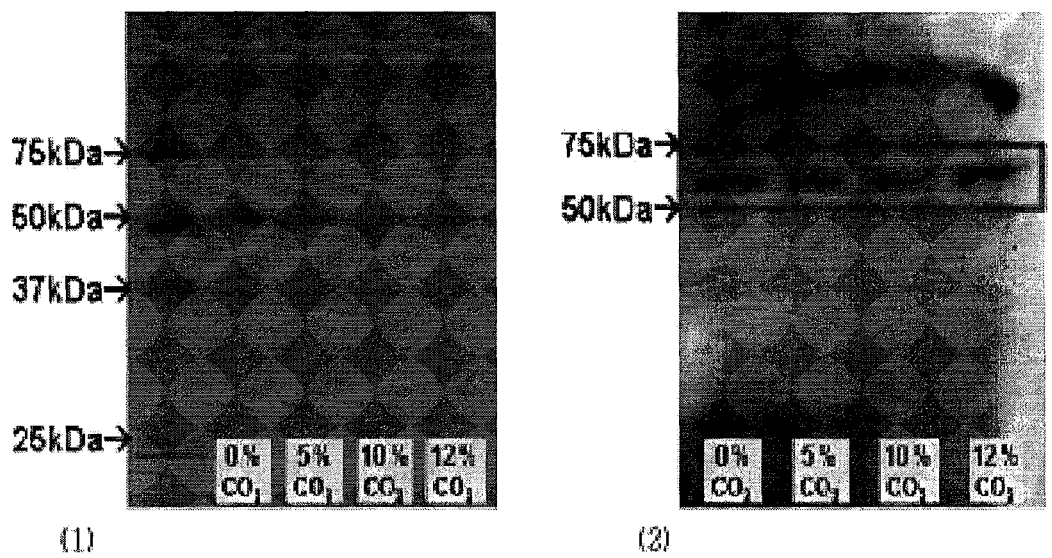
FIG. 6 shows the results of performing Western blot analysis using α-carbonic anhydrase antibody in order to measure the change in expression of carbonic anhydrase in the microalgae of the present invention.

As can be seen in FIG. 6, when the α-carbonic anhydrase of *Dunaliella* microalgae was used as a probe, a protein band inferred to be the carbonic anhydrase of the microalgae of the present invention could be confirmed. Particularly, through the above experimental results, it could be seen that the α-carbonic anhydrase was continuously expressed regardless of the concentration of carbon dioxide.

As described above, it could be seen that the microalgae of the present invention expressed carbonic anhydrase at a substantially constant level regardless of the concentration of carbon dioxide, and as can be seen in the results of Example 2-1, the Km value significantly changed depending on the concentration of carbon dioxide. This suggests that the microalgae of the present invention can be effectively cultured even at high carbon dioxide concentrations.

Example 4

Evaluation of Carbon Dioxide Fixation Ability According to Mass Culture of Inventive Microalgae To a 30-L photo-bioreactor (Liflus G P, Biotron, Korea) which has been widely used in the prior art, carbon dioxide was supplied at a concentration of 0%, 5% or 10% or, captured flue gas containing 10% carbon dioxide was supplied. For the culture of the microalgae in the bioreactor, BG-11 medium was used, the flow rate of carbon dioxide or flue gas was set at 0.1 VVM, and conditions of 20° C. and light dose of 25 μE/($m^2$s) were used. The initial inoculation concentration of the inventive microalgae was set at $1 \times 10^6$ cells/mL.

Figure 7:
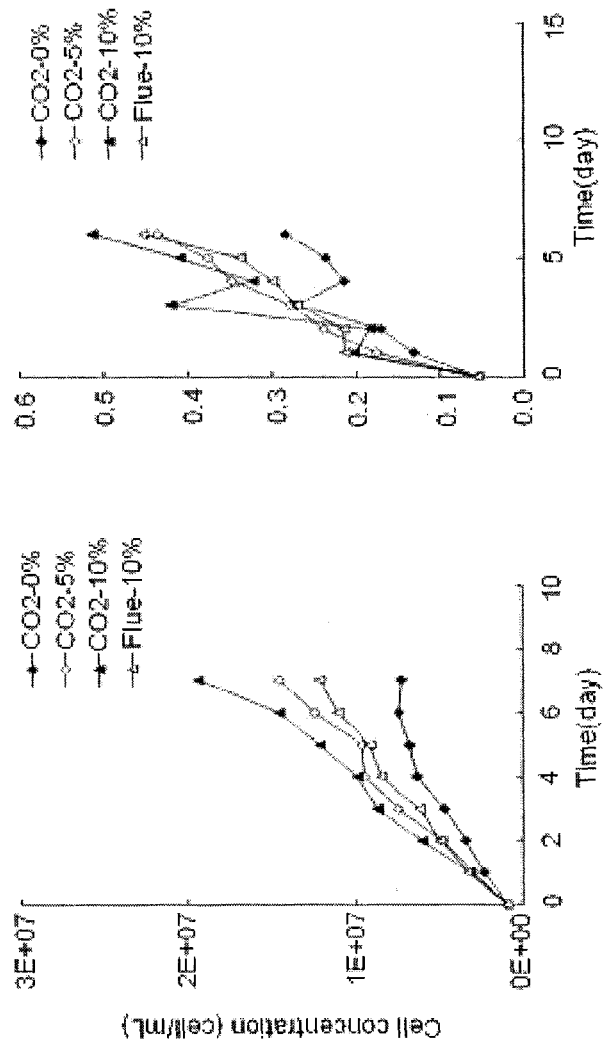
FIG. 7 is a set of graphs showing the results of culturing the microalgae of the present invention in a photo-bioreactor and measuring the cell number and weight of the cultured microalgae.

During the culture process, the number and weight of the cells according to the concentration of carbon dioxide were measured, and the results of the measurement are shown in FIG. 7.

As shown in FIG. 7, the number and fresh weight of the cells increased as the concentration of carbon dioxide increased, and in the case of flue gas, the number of the cells increased by 63% compared to the case in which carbon dioxide was supplied at a concentration of 10%, and the fresh cell weight was about 80% compared to that case. This was believed to be because of NOx or SOx contained in the flue gas, but it was thought that NOx or SOx do not greatly interfere with the growth of cells.

In addition, during the culture process, the carbon dioxide fixation rate of the microalgae according to the concentration of carbon dioxide was measured, and the results of the measurement are shown in Table 8 below.

TABLE 8

Carbon dioxide fixation ability (unit: mmol/L/hr) in mass culture of microalgae using photo-bioreactor

| Number of experiments | $CO_2$-0% | $CO_2$-5% | $CO_2$-10% | Flue gas |
|---|---|---|---|---|
| 1 | 0.146 | 0.231 | 0.282 | 0.302 |
| 2 | 0.191 | 0.076 | 0.454 | 0.105 |
| 3 | 0.042 | 0.057 | 0.167 | 0.074 |
| 4 | 0.091 | 0.112 | 0.200 | 0.221 |
| 5 | 0.010 | 0.114 | 0.241 | 0.091 |

As can be seen in Table 8 above, the microalgae of the present invention had a high carbon dioxide fixation rate even when they were cultured in large amounts using the photo-bioreactor. This suggests that the microalgae of the present invention can effectively remove carbon dioxide even if they are industrially applied in practice.

The invention claimed is:

1. Cosmetics comprising an isolated strain of *Scenedesmus producto-capitatus microalga*, deposited in Korean Collection of Type Culture under accession number KCTC1136BP.

\* \* \* \* \*